United States Patent

Tognella et al.

[11] Patent Number: 5,300,671
[45] Date of Patent: Apr. 5, 1994

[54] GEM-DIPHOSPHONIC ACIDS, AND PHARMACEUTICAL COMPOSITIONS CONTAINING THEM

[75] Inventors: Sergio Tognella; Valeria Livi; Ernesto Menta; Silvano Spinelli, all of Milan, Italy

[73] Assignee: Boehringer Mannheim Italia S.p.A., Milan, Italy

[21] Appl. No.: 847,067

[22] PCT Filed: Oct. 11, 1990

[86] PCT No.: PCT/EP90/01710
§ 371 Date: Jun. 9, 1992
§ 102(e) Date: Jun. 9, 1992

[87] PCT Pub. No.: WO91/05791
PCT Pub. Date: May 2, 1991

[30] Foreign Application Priority Data
Oct. 12, 1989 [IT] Italy ................. 22004 A/89

[51] Int. Cl.⁵ ............... C07F 9/40; C07F 9/38
[52] U.S. Cl. .................. 558/159; 558/161; 562/13
[58] Field of Search ......... 558/159, 161; 562/13; 514/107

[56] References Cited

U.S. PATENT DOCUMENTS 4,608,368 8/1986 Blum et al. .................. 514/107
4,666,895 5/1987 Bosies et al. ................ 514/108

FOREIGN PATENT DOCUMENTS

3425812A1 1/1986 Fed. Rep. of Germany.

OTHER PUBLICATIONS

Journal of The National Cancer Institute, "Nude Rat Model for Studying Metastasis of Human Tumor Cells to Bone and Bone Marrow" vol. 82, No. 5, Mar. 7, 1990, pp. 408–412.
Effects of New Bisphosphonic Acids on Tumor-Induced Bone Destruction in the Rat, J. Cancer Res clin Oncol (1986) 111:335–341.
"Protective Effects of a Prophylactic Treatment with the Bisphosphonate 3-Amino-1-Hydroxypropane-1,-1-Bisphosphonic Acid on the Development of Tumor Osteopathies in the Rat: Experimental Studies with the Walker Carcinosarcoma 256[1]," Oncology 45: 41–46 (1988).
Chemical Abstracts, vol. 109, No. 17, Oct. 24, 1988.
Wingen, F. et al. *J. Cancer Res. Clin. Oncol.* 1986, 111, 209–219.
Marmonti et al. *Clinical and Experimental Metastasis* vol. 10, Suppl. 1, pp. 53–54, Aug. 1992.
Nakai et al. *Cancer Res.* 53, 5395–5399 (1992).

Primary Examiner—Mary C. Lee
Assistant Examiner—M. Ambrose
Attorney, Agent, or Firm—Nikaido, Marmelstein Murray & Oram

[57] ABSTRACT

Diphosphonic acids of formula (I), wherein $R_1$ and $R_2$ are hydrogen or $C_1$-$C_4$ alkyl; (A) is hydrogen, halogen, hydroxy or $C_1$-$C_{12}$ alkyl; (B) is a bond, a $C_1$-$C_8$ alkylene chain, a cycloalkylalkylene chain, an alkylene chain substituted by cyclohexyl or cyclopentyl groups, or an aralkyl chain, an alkyl chain containing an heteroatom (O, S or N—$CH_3$) or an ureido residue —$(CH_2)_{nl}$—NH-CONH—$(CH_2)_n$—with n ranging from 1 to 5, $R_3$ is hydrogen, $C_1$-$C_9$ alkyl, $C_3$-$C_6$ cycloalkyl, benzyl, phenyl or p-methoxybenzyl; (C) is $C_1$-$C_5$ alkyl, phenyl or an aralkyl chain; $R_4$ is hudrogen, $C_1$-$C_5$ alkyl or an amino group optionally substituted by alkyl, phenyl, benzyl, p-methoxybenzyl, acyl, amminoacidic or peptide groups; $R_5$ and $R_6$ are 2-haloethyl or together form a 1-aziridinyl residue, are useful as antitumor agent.

11 Claims, No Drawings

GEM-DIPHOSPHONIC ACIDS, AND PHARMACEUTICAL COMPOSITIONS CONTAINING THEM

The present invention relates to diphosphonic acids having antitumor activity, a process for the preparation thereof and pharmaceutical compositions containing them.

Gem-diphosphonic acids and the salts thereof are known and used in the treatment of osteoporosis and bone resorption (EP 96.931, EP 252.504, BE 896.453, BE 903.519, DE 3.016.289, DE 3.540.150, DE 2.534.391). Moreover, diphosphonic acid esters having pesticide activity are disclosed in U.S. Pat. No. 3.906.062. However, no compounds described in the above mentioned patents have been reported to have intrinsic antitumor activity.

DE 3.425.812 discloses 1,1-diphosphonic acid derivatives having a bis[(haloalkyl)amino]phenyl residue as agents useful for the treatment of bone tumours. In fact, beside having the bone tropism characteristic of diphosphonic acids, they also have the typical cytotoxic activity of molecules bearing dialkylating functions.

It has now been found that diphosphonic acid derivatives characterized by the presence of a bond which can be physiologically hydrolyzed, connecting the diphosphonic derivative with a dialkylating residue, have, compared with the above cited compounds, advantageous antitumor and antimetastatic properties, which could not be predicted on the basis of their chemical structure and of the presumed bioconversion thereof into the separate components (diphosphonic derivative and alkylating derivative).

The present invention, therefore, provides compounds of formula (I)

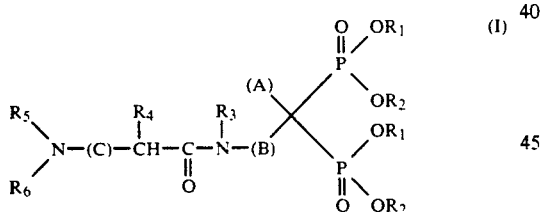

wherein:
$R_1$ and $R_2$, which can be the same or different, are hydrogen or $C_1-C_4$ alkyl;
(A) is hydrogen, halogen (chlorine, bromine or iodine), hydroxy, straight or branched $C_1-C_{12}$ alkyl;
(B) is a covalent bond, a straight or branched $C_1-C_8$ alkylene or, together with the adjacent nitrogen atom, a group of formula

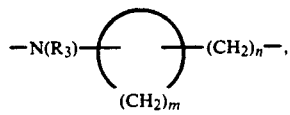

therein the groups —N($R_3$)— and —(CA$_2$)$_n$— may be in the 1,1; 1,2; 1,3 or 1,4 position of the ring; an ortho, meta or para -substituted aralkylene of formula

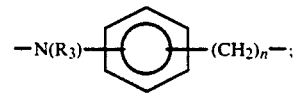

an alkylene chain containing at least one heteroatom of formula —[CH(CH$_3$)]$_p$—(CH$_2$)$_{n_1}$—X—(CH$_2$)$_n$—; m is the integer 5 or 6; n and n$_1$ are an integer from 1 to 5; p is zero or 1 and X is O, S,

or the ureido group —NH—CO—NH—; $R_3$ is hydrogen, straight or branched $C_1-C_9$ alkyl, $C_3-C_6$ cycloalkyl, benzyl, phenyl or p-methoxybenzyl;
(C) is straight or branched $C_1-C_5$ alkyl, phenylene, an aralkylene chain of formula

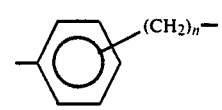

in which n is as above defined;
$R_4$ is hydrogen, straight or branched $C_1-C_4$ alkyl, or it is a group of formula

in which $R_7$ and $R_8$, which are the same or different, are hydrogen, straight or branched $C_1-C_6$ alkyl, phenyl, benzyl, p-methoxybenzyl, or one of $R_7$ and $R_8$ is as above defined and the other one is a group of formula

in which $R_9$ is hydrogen, straight or branched $C_1-C_4$ alkyl, phenyl, benzyl, p-methoxyphenyl, straight or branched $C_1-C_4$ alkoxy, halo-$C_1-C_4$-alkoxy; $R_5$ and $R_6$ are haloethyl (2-chloroethyl, 2-bromoethyl, 2-iodoethyl) or $R_5$ and $R_6$, together with the nitrogen atom to which they are bound, are a 1-aziridinyl residue of formula

The present invention also includes racemic and diastereoisomeric mixtures as well as the single enantiomers and diastereoisomers of the compounds of formula (I).

The present invention further comprises the pharmaceutically acceptable salts of the compounds of formula (I), for example with inorganic bases, such as the salts with alkali metals (e.g. sodium or potassium) or with alkaline-earth metals (e.g. calcium or magnesium), or the ammonium salts; the salts with organic bases, such as methylamine, ethylamine, propylamine, isopropylamine, butylamine, t-butylamine, dimethylamine, diethylamine, diethanolamine, trimethylamine, triethylamine, piperidine, pyridine, picoline, dicyclohexylamine; the organic acid addition salts, such as: formate, acetate, trifluoroacetate, maleate, fumarate, tartrate, methanesulfonate, benzenesulfonate, toluenesulfonate salts; the inorganic acid addition salts, such as hydrochloride, hydrobromide, sulphate, hydrogen sulphate, phosphate salts; or the salts with amino acids, such as aspartates, glutamates or the salts with lysine or arginine.

$C_1$–$C_4$ Alkyl includes methyl, ethyl, n-propyl, isopropyl, n-butyl, t-butyl or isobutyl; particularly preferred are methyl and ethyl. The $C_1$–$C_{12}$ alkyl group can be, beside the meanings above precised for $C_1$–$C_4$ alkyl, n-pentyl, n-hexyl, n-decyl and the like; particularly preferred are methyl and ethyl. The alkylene chain (B) is preferably —$(CH_2)_q$—, wherein q is an integer from 2 to 5,

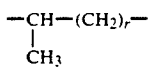

wherein r is an integer from 2 to 5, or one of the groups of formulae

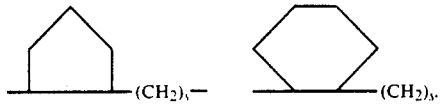

wherein s is an integer from 1 to 4.

$R_3$ is preferably hydrogen or methyl, whilst (C) is preferably benzyl or

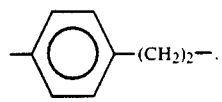

When (C) is benzyl, $R_4$ is preferably a group of formula

wherein $R_7$ and $R_8$ are preferably hydrogen, or one of them is $R_9$—CO— wherein $R_9$ is hydrogen, methyl, tert-butoxy, trichloromethoxy, (2,2,2)trichloroethoxy, benzyloxy, ethoxy.

When (C) is a residue of formula

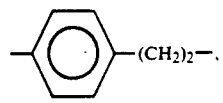

$R_4$ is preferably hydrogen.

$R_5$ and $R_6$ are preferably 2-chloroethyl.

The compounds according to formula (I) are prepared by reaction of a compound of formula (II)

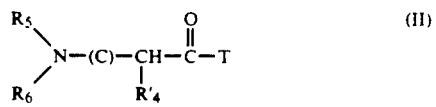

wherein $R_5$, $R_6$ and (C) are as above defined and $R'_4$ is the same as $R_4$ or a group which can be transformed into $R_4$ by removal of any protecting groups present, T is hydroxy or a group which activates the carboxylic function with a compound of formula (III)

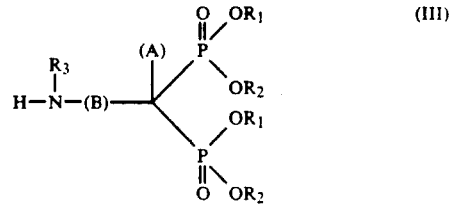

wherein $R_1$, $R_2$, $R_3$, (A) and (B) are as above defined, to give a compound of formula (Ia)

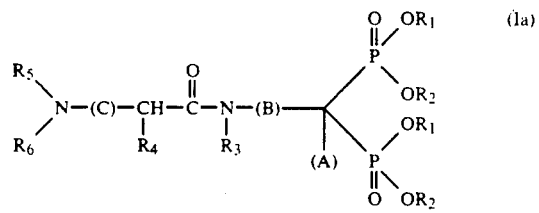

wherein $R_1$, $R_2$, $R_3$, $R_4$, $R_5$, $R_6$, (C), (B) and (A) are as above defined, which compound can in its turn be transformed into a compound of formula (I) by means of well-known reactions for the selective elimination of the protecting groups, or by alkylating or acylating the amino groups, and the like.

When in the reaction of compounds (III) with compounds (II) the latter are used in form of carboxylic acids (T=OH), the reaction is generally carried out in the presence of a condensing agent such as N,N'-dicyclohexylcarbodiimide, N-cyclohexyl-N'-morpholinoethylcarbodiimide, N-ethyl-N'-(3-dimethylaminopropyl)carbodiimide; N,N'-carbonyl-bis(imidazole); phosphorus oxychloride; phosphorus trichloride; thionyl chloride; oxalyl chloride; ethyl chloroformate; isobutyl chloroformate; morpholinoethylisonitrile and the like. Examples of activated forms of carboxylic acids, according to formula (III), are acid halides, symmetrical or mixed anhydrides (e.g. with methanesulfonic, acetic, isobutyric, pivalic, trichloroacetic acids); activated amides (e.g. with imidazole or triazole); acylazide; activated esters (e.g. p-nitrophenyl ester, methoxymethyl ester, 2,4-dinitrophenyl ester, pentachlorophenyl ester, hydroxysuccinimido ester, 1-hydroxy-2-(1H)-pyridone ester, 1-hydroxybenzotriazole ester) and the like. The reaction can be carried out in the presence of an inorganic base, such as an alkali carbonate or hydrogen carbonate, an alkaline or alkaline-earth hydroxide or an organic base, such as triethylamine, tributylamine, pyridine, dimethylaminopyridine, N-alkylmorpholine, N,N-dialkyl-aniline and the like.

The reaction can be carried out at a temperature ranging from −40° C. to the reflux temperature of the solvent, preferably using a slight molar excess of compound (II) to compound (III), in a solvent such as water, pyridine or N,N-dimethylformamide or mixtures thereof.

The reaction temperature preferably ranges from $-10°$ C. to room temperature and the reaction time ranges from 1 to 48 hours, but generally the reaction is complete within 2-12 hours.

Alternatively, the mixed anhydrides or the acid chlorides of the compounds of formula (II) can be reacted with the compounds of formula (III) in heterogeneous phase, in a solvent such as an ester, e.g. methyl or ethyl formates; ethyl, methyl or isopropyl acetates; or in a halogenated solvent such as dichloromethane or chloroform, or in a straight or cyclic ether such as dioxane, tetrahydrofuran, ethyl ether, tert-butylmethyl ether and mixtures thereof. Temperature conditions and reaction times are the same as above reported.

Compounds of general formula (II) are known compounds, which are commercially available and/or can be prepared by means of conventional methods, such as those described in: J. Med. Chem. 24, 1304, (1981); CA 51: 8066d, (1957); BE 905,974; CA 104: 141897 (1986); J. Med. Chem. 7, 468, (1964); J. Med. Chem. 6, 85, (1963); Cancer Chem. Rep. 50, 685, (1966); J. Med. Chem. 21, 16, (1977); J. Org. Chem. 26, 1554, (1961); J. Org. Chem. 26, 1674, (1961); CA 64: 10267g, (1966); J. Chem. Soc., 2994, (1960); Biochem. Pharmacol. 11, 847, (1962); Biochem. Pharmacol. 12, 833, (1963); CA 73: 131293c, (1970); Biochem. Pharmacol. 5, 192, (1960).

Compounds of general formula (III) are also known and/or can be prepared according to known methods. See, for instance, EP 96,931, EP 252,504, BE 903,519, DE 3,016,289, EP 224,751, DE 2,534,391, EP 197,478.

If desired, compounds of general formula (I) wherein $R_1$ and $R_2$ are different from hydrogen, can optionally be transformed into the corresponding gem-diphosphonic acids by treatment with a molar excess of trialkylsilyl-chloride, -iodide or -bromide in a halogenated solvent such as dichloromethane, 1,2-dichloroethane, 1,1,2-trichloroethane and the like. Trimethylsilyl iodide is preferably used.

The reaction times ranges from a few minutes to 72 hours; the reaction temperatures range from 0° C. to the solvent's reflux temperature; preferred reaction conditions are those according to J. Org. Chem: 28, 2975–78, (1963).

The removal of the secondary- or primary-amine protecting groups optionally present in the compounds of general formula (I) can be carried out according to well-known techniques, particularly those used in peptide synthesis.

The compounds of the invention have high cytotoxic activity against tumour cells, as it can be evidenced by means of "in vitro" tests carried out, for instance, according to the procedure described by M. P. Hacker, Cancer Res. 45, 4748, (1985). The $ID_{50}$ (i.e. the compound dose which can inhibit by 50% the growth of "in vitro" cultured murine and human tumour cells of both solid and hematic tumors) of the compounds of the invention were found to be comprised from 0.1 to 5 $\mu g/ml$ of culture medium. Under these test conditions, the compounds of the invention: N-{4-[bis(2-chloroethyl)amino]phenyl-(L)-alanyl}-5-amino-1-hydroxypentane-1,1-diphosphonic acid monohydrochloride and N-{4-[bis(2-chloroethyl)amino]phenyl-butirroyl}-4-amino-1-hydroxy-butane-1,1-diphosphonic acid have an $ID_{50}$ of 0.1 $\mu g/ml$ and 0.5 $\mu g/ml$, respectively, against murine leukemia L1210.

"In vitro" studies on the compound of the invention N-{4-[bis(2-chloroethyl)amino]phenyl-(L)-alanyl}-4-amino-1-hydroxy-butane-1,1-diphosphonic, using different human tumor cell lines (for example fibrosarcoma HT 1080, osteosarcoma H2-OS etc.) showed $ID_{50}$ ranging from 13.6 to 16.5 $\mu g/ml$; the substance appears to be less cytotoxic than the related starting material 4-amino-1-hydroxy-1,1-diphosphonic acid, whose $ID_{50}$ range from 2.7 to 8.2 $\mu/ml$.

The same compound, when tested "in vivo" by i.v. administration (on days 2—6—9—13 after tumor implantation) in rats bearing Walker B mammary carcinoma (implanted on day 0 intramuscolarly $10^6$ cells) causes complete regression of tumor growth combined with normalization of tumor induced hypercalcemia. Under the same experimental conditions, the related starting diphosphonate (i.e. 4-amino-1-hydroxy-butane-1,1-diphosphonic acid) even if endowed with higher "in vitro" cytotoxicicy, is surprisingly ineffective in retarding tumor growth, also when administered at its maximum tolerated dosage.

The compounds of the invention are characterized by a low acute toxicity and are well tolerated by the animals.

The compounds of the invention have a high therapeutical index, in light of the low toxicity and the effective antitumor activity thereof. Moreover, the high water-solubility of the compounds of the present invention allows the easy preparation of parenteral and oral pharmaceutical forms.

The compounds of formula (I), when administered to humans and animals affected with tumours which can be treated with alkylating agents, at doses ranging from 1 mg to 1.2 g/m² body area, can induce the regression of the above mentioned tumoral forms.

The effective dosage for the compounds of the invention can be determined by the expert clinicians according to conventional methods. The relationship between the dosages used for various animal species and those for humans (on the basis of mg/m² body area) is described by Freireich, E. J., et al., "Quantitative Comparison of Toxicity of Anticancer Agents in Mouse, Rat, Hamster, Dog, Monkey and Man", *Cancer Chemother. Rep.*, 50, n. 4, 219–244, May 1966.

Nevertheless, the patient will be administered generally with doses from 1 to 1,200 mg/kg body weight of the compounds of the invention, with a dosage regimen which will vary depending on various factors, which are well known to the expert clinicians.

Some compounds of the invention may have such an high toxicity, or such an unfavourable therapeutical index, so as to be unsuited for an antitumor treatment in the patients. Nevertheless, those parameters can easily be determined by means of conventional toxycological tests, such as acute and subacute $DL_{50}$ in mouse. Of course, those compounds which turn out to be toxic will be avoided.

The compounds of the invention will be used in the treatment of those tumours which can be treated with alkylating agents.

Particularly, multiple myeloma, osteosarcoma; bone-metastasis; breast, ovarian and testis carcinomas can also be advantageously treated.

Moreover, the compounds of the invention can advantageously be used in the therapy of other solid and hematic neoplasias, such as lymphomas and leukemias in humans and animals, according to treatment protocols which can be easily determined by those skilled in the art.

The compounds of the invention are preferably administered by the intravenous or intraarterial routes, even though other administration forms can be envisaged in particular cases.

The pharmaceutical forms which can be used for parenteral administration include sterile aqueous solutions or sterile powders for the extemporary preparation of solutions, as well as oily preparations for intramuscular or intraperitoneal administrations.

Other useful pharmaceutical forms are syrups or similar liquid forms, as well as solid forms such as tablets, capsules and the like.

The following examples illustrate the invention in more detail.

EXAMPLE 1 a) A solution of bis(tert-butoxy)carbonate (450 mg) in tetrahydrofuran (THF; 4 ml) is quickly added to a solution of 4-[bis(2-chloroethyl)amino]-(L)-phenylalanine (300 mg) in THF (10 ml) and 1N NaOH (1 ml).

The resulting mixture is stirred at room temperature for 2 hours, adjusting pH to about 9 by repeated additions of 1N NaOH. Then the solvent is removed under vacuum and the residue is partitioned between water (3 ml) and ethyl ether (5 ml).

The organic phase is discharged and the aqueous one is acidified with HCl and repeatedly extracted with ethyl ether. The combined organic extracts are dried over $Na_2SO_4$ and evaporated to dryness under vacuum, to obtain a foamy residue of N'-(tert-butoxycarbonyl)-4-[bis(2-chloroethyl)amino]-(L)phenylalanine (290 mg).

NMR ($CDCl_3$, TMS) $\delta = 1.4$ (s, 9H); 3.1 (m, 2H); 3.65 (m 8H); 4.55 (m, 1H); 4.99 (d, 1H); 6.62 (d, 2H); 7.12 (d, 2H); 8.1 (s, 1H).

b) N-Hydroxysuccinimide (173 mg) and morpholinoethylisonitrile (0.133 ml) are added to a solution of the compound from step a) (290 mg). The mixture is stirred at room temperature for one hour, then concentrated to dryness under vacuum. The residue is taken up into 2N HCl (5 ml) and repeatedly extracted with ethyl ether (3×5 ml). The organic phases are collected, washed with 5% aqueous $NaHCO_3$; with water (5 ml) and then dried over $Na_2SO_4$. Upon removing the solvent under vacuum, an oily residue is obtained which is crystallized from an ethyl ester—isopropyl ether mixture to give 260 mg of N'-(tert-butoxycarbonyl)-4-[bis(2-chloroethyl)amino]-(L)-phenylalanine hydroxysuccinimido ester, melting point 140°–143° C.;

NMR (TMS, $CDCl_3$) $\delta = 1.45$ (s, 9H); 2.85 (s, 4H); 3.15 (m, 2H); 3.69 (m, 8H); 4.9 (m, 1H); 6.61 (d, 2H); 7,15 (d, 2H).

c) A solution of the obtained activated ester (50 mg) in dimethylformamide (DMF, 2.5 ml) is slowly dropped into a solution of 5-amino-1-hydroxypentane-1,1-diphosphonic acid (21.8 mg) dissolved in a mixture of water (2.5 ml), 1N NaOH (0.331 ml) and DMF (2 ml). DMF is added to the reaction mixture simultaneously to the ester solution, until complete dissolution of the reagents is obtained (2.5 ml).

The obtained slightly opalescent solution is centrifuged; the supernatant liquid is collected and concentrated under reduced pressure. The residue is diluted with DMF (5 ml) to separate a precipitate which is collected by centrifugation and washed with ethyl acetate, yielding 35 mg of N-{N'-(tert-butoxycarbonyl)-4-[bis(2-chloroethyl)amino]-(L)-phenylalanyl}-5-amino-1-hydroxypentane-1,1-diphosphonic acid trisodium salt, m.p. >260° C.

NMR (TMS, $D_2O$): $\delta 1.3$ (s, 9H); 1.4–1.7 (m, 4H); 1.8–2.05 (m, 2H); 2.62–3.1 (m, 2H); 3.2 (t, 2H); 3.75 (s, 8H); 4.2 (t, 1H); 6.85 (d, 2H); 7.15 (d, 2H).

EXAMPLE 2

Following the same procedure as described in Example 1, by reacting N'-(tertbutoxyarbonyl)-4-8 bis-(2-chloroethyl)amino]-(L)-phenylalanine hydroxysuccinimido ester with the appropriate aminoalkyl-1-hydroxy-1,1-diphosphonic acids, the following compounds are obtained:

N-{N'-(tert-butoxycarbonyl)-4-[bis(2-chloroethyl)amino]-(L)-phenylalanyl}-4-amino-1-hydroxybutane-1,1-diphosphonic acid (trisodium salt), NMR ($D_2O$, TMS): $\delta = 1.3$ (s, 9H); 1.6 (m, 2H), 1.92 (m, 2H); 2.62÷3.1 (m, 2H); 3.2 (t, 2H); 3.75 (s, 8H); 4.2 (t, 1H); 6.8 (d, 2H); 7.15 (d, 2H);

N-{N'-(tert-butoxycarbonyl)-4-[bis(2-chloroethyl)amino]-(L)-phenylalanyl}-3-amino-1-hydroxypropane-1,1-diphosphonic acid (trisodium salt), NMR ($D_2O$, TMS): $\delta = 1.32$ (s, 9H); 2.1 (m, 2H), 2.65÷3.1 (m, 2H); 3.21 (m, 2H); 3.75 (s, 8H); 4.2 (t, 1H); 6.8 (d, 2H); 7.15 (d, 2H);

N-{N'-(tert-butoxycarbonyl)-4-[bis(2-chloroethyl)amino]-(L)-phenylalanyl}-6-amino-1-hydroxyhexane-1,1-diphosphonic acid (trisodium salt), NMR ($D_2O$, TMS): $\delta = 1.3$ (s, 9H); 1.5 (m, 2H), 1.6 (m, 4H); 1.9 (m, 2H); 2.65÷3.1 (m, 2H); 3.20 (t, 2H); 3.75 (s, 8H); 4.2 (t, 1H); 6.8 (d, 2H); 7.15 (d, 2H);

N-{N'-(tert-butoxycarbonyl)-4-[bis(2-chloroethyl)amino)]-(L)-phenylalanyl}-4-amino-1-hydroxypentane-1,1-diphosphonic acid (trisodium salt).

NMR ($D_2O$, TMS): $\delta = 1.32$ (s, 9H); 1.4 (d, 3H), 1.7 (m, 2H); 1.9 (m, 2H); 2.6÷3.05 (m, 2H); 3.15 (d, 1H); 3.75 (s, 8H); 4.2 (t, 1H); 6.85 (d, 2H); 7.15 (d, 2H);

N-{N'-(tert-butoxycarbonyl)-4-[bis(2-chloroethyl)amino]-(L)-phenylalanyl}-3-(2-aminocyclopent-1-yl)-1-hydroxypropane-1,1-diphosphonic acid (trisodium salt), NMR ($D_2O$, TMS): $\delta = 1.3$ (s, 9H); 1.42÷1.75 (m, 9H), 1.9 (m, 2H); 2.62÷3.1 (m, 2H); 3.3 (m, 1H); 3.75 (s, 8H); 4.2 (t, 1H); 6.85 (d, 2H); 7.15 (d, 2H);

N-{N'-(tert-butoxycarbonyl)-4-[bis(2-chloroethyl)amino]-(L)-phenylalanyl}-4-amino-4,4-pentamethylene-1-hydroxybutane-1,1-diphosphonic acid (trisodium salt), NMR ($D_2O$, TMS): $\delta = 1.3$ (s, 9H); 1.55 (m, 10H), 1.6 (m, 2H); 1.9 (m, 2H); 2.62÷3.1 (m. 2H); 3.75 (s, 8H); 4.2 (t, 1H); 6.85 (d, 2H); 7.15 (d, 2H);

N-methyl-N-{N'-(tert-butoxycarbonyl)-4-[bis(2-chloroethyl)amino]-(L)-phenylalanyl}-5-amino-1-hydroxypentane-1,1-diphosphonic acid (trisodium salt), NMR ($D_2O$, TMS): $\delta = 1.3$ (s, 9H); 1.55 (m, 4H), 1.9 (m, 2H); 2.1 (m, 3H); 2.62÷3.1 (m, 2H); 3.2 (t, 2H); 3.75 (s, 8H); 4.2 (t, 1H); 6.85 (d, 2H); 7.15 (d, 2H);

N-{N'-(tert-butoxycarbonyl)-4-[bis(2-chloroethyl)amino]-(L)-phenylalanyl}-4-amino-1-tetramethylene-1-hydroxybutane-1,1-diphosphonic acid (trisodium salt), NMR ($D_2O$, TMS): $\delta = 1.3$ (s, 9H); 1.5 (m, 8H), 1.6 (m, 2H); 1.9 (m, 2H); 2.62÷3.1 (m, 2H); 3.75 (s, 8H); 4.2 (t, 1H); 6.85 (d, 2H); 7.15 (d, 2H);

EXAMPLE 3

Following the same procedure as described in Example 1b), by reacting 4-[4-[bis(2-chloroethyl)amino]- phenyl]butyric acid (300 mg) with N-hydroxysuccinimide (245 mg) and N-morpholinoethylisonitrile (0.18 ml), 4-[4-[bis(2-chloroethyl)amino]phenyl]butyric acid N-hydroxysuccinimido ester (360 mg) is prepared, m.p. 80°–82° C.

Following the same procedure as described in Example 1c), the above hydroxysuccinimido ester (112 mg) is reacted with 5-amino-1-hydroxypentane-1,1-diphosphonic acid (61.2 mg) to obtain N-{4-[4-[bis(2-chloroethyl)amino]phenyl]butyroyl}-5-amino-1-hydroxypentane-1,1-diphosphonic acid trisodium salt (80 mg), m.p. >260° C.

NMR (TMS, D$_2$O): δ=1.4–1.7 (m, 4H); 1.8÷2.05 (m, 4H); 2.15 (t, 2H); 2.55 (t, 2H); 3.18 (t, 2H); 3.75 (s, 8H); 6.8 (d, 2H); 7.15 (d, 2H);

HPLC: Partisfere® C$_{18}$, 150×4.6 mm; 0.025M sodium heptanesulfonate in water/acetonitrile/dioxane 70:20:10, pH ~2.5 with H$_3$PO$_4$; flow: 1.3 ml/min; λ=255 nm. Retention time: 6.86'.

EXAMPLE 4

Following the procedure described in Example 3, by reacting N-4-[4-[bis(2-chloroethyl)amino]phenyl]-butyric acid hydroxysuccinimido ester with the appropriate aminoalkyl-1-hydroxy-1,1-diphosphonic acids, the following compounds are obtained:

N-{4-[4-[bis (2-chloroethyl)amino]phenyl]butyroyl}-4-amino-1-hydroxybutane-1,1-diphosphonic acid (trisodium salt), NMR (TMS, D$_2$O): δ=1.7÷2.05 (m, 6H); 2.25 (t, 2H); 2.55 (t, 2H); 3.18 (t, 2H); 3.75 (s, 8H); 6.85 (d, 2H); 7.2 (d, 2H);

HPLC: Partisfere® C$_{18}$, 150×4.6 mm; 0.025M sodium heptanesulfonate in water/acetonitrile/dioxane 70:20:10, pH ~2.5 with H$_3$PO$_4$; flow 1.3 ml/min.; λ=255 nm. Retention time: 5.96'.

N-{4-[4-[bis (2-chloroethyl)amino]phenyl]butyroyl}-3-amino-1-hydroxypropane-1,1-diphosphonic acid (trisodium salt), NMR (TMS, D$_2$O): δ=1.8÷2.05 (m, 4H); 2.25 (t, 2H); 2.55 (t, 2H); 3.18 (t, 2H); 3.75 (s, 8H); 6.8 (d, 2H); 7.15 (d, 2H);

N-{4-[4-[bis (2-chloroethyl)amino]phenyl]butyroyl}-6-amino-1-hydroxyhexane-1,1-diphosphonic acid (trisodium salt), NMR (TMS, D$_2$O): δ=1.4 (m, 2H); 1.6 (m, 4H); 1.9 (m, 4H); 2.25 (t, 2H); 2.55 (t, 2H); 3.18 (t, 2H); 3.75 (s, 8H); 6.8 (d, 2H); 7.15 (d, 2H);

N-{4-[4-[bis (2-chloroethyl)amino]phenyl]butyroyl}-4-amino-1-hydroxypentane-1,1-diphosphonic acid (trisodium salt), NMR (TMS, D$_2$O): δ=1.4 (d, 3H); 1.7 (m, 2H); 1.9 (m, 4H); 2.25 (t, 2H); 2.55 (t, 2H); 3.18 (d, 1H); 3.75 (s, 8H); 6.85 (d, 2H); 7.2 (d, 2H);

N-{4-[4-[bis (2-chloroethyl)amino]phenyl]butyroyl}-3-(2-aminocyclopent-1-yl)-1-hydroxypropane-1,1-diphosphonic acid (trisodium salt), NMR (TMS, D$_2$O): δ=1.42÷1.75 (m, 9H); 1.9 (m, 4H); 2.25 (t, 2H); 2.55 (t, 2H); 3.2 (m, 1H); 3.75 (s, 8H); 6.8 (d, 2H); 7.15 (d, 2H);

N-{4-[4-[bis (2-chloroethyl)amino]phenyl]butyroyl}-4-amino-4,4-pentamethylene-1-hydroxybutane-1,1-diphosphonic acid (trisodium salt), NMR (TMS, D$_2$O): δ=1.55 (m, 10H); 1.6 (m, 2H); 1.9 (m, 4H); 2.15 (t, 2H); 2.55 (t, 2H); 3.75 (s, 8H); 6.8 (d, 2H); 7.15 (d, 2H);

N-methyl-N-{4-[4-[bis (2-chloroethyl)amino]phenyl]-butyroyl}-5-amino-1-hydroxypentane-1,1-diphosphonic acid (trisodium salt), NMR (TMS, D$_2$O): δ=1.55 (m, 4H); 1.9 (m, 4H); 2.1 (s, 3H); 2.15 (t, 2H); 2.55 (t, 2H); 3.18 (t, 2H); 3.75 (s, 8H); 6.8 (d, 2H); 7.15 (d, 2H);

N-{4-[4-[bis (2-chloroethyl)amino]phenyl]butyroyl}-4-amino-4,4-tetramethylene-1-hydroxybutane-1,1-diphosphonic acid (trisodium salt), NMR (TMS, D$_2$O): δ=1.5 (m, 8H); 1.7÷2.05 (m, 6H); 2.15 (t, 2H); 2.55 (t, 2H); 3.75 (s, 8H); 6.8 (d, 2H); 7.15 (d, 2H);

EXAMPLE 5

A solution of N-{N'-(tert-butoxycarbonyl)-4-[bis(2-chloroethyl)amino]-(L)-phenylalanyl}-5-amino-1-hydroxypentane-1,1-diphosphonic acid trisodium salt (35 mg) in methanol saturated with hydrochloric acid (2 ml) is heated to 40°–50° C. for 4 hours, then the solution is concentrated to reduced volume and the precipitated sodium chloride is filtered. The filtrate is evaporated to dryness and the residue is triturated with acetone and filtered. After recrystallization from ethanol/ethyl ether, N-{4-[bis(2-chloroethyl)amino]-(L)-phenylalanyl}-5-amino-1-hydroxypentane-1,1-diphosphonic acid monohydrochloride (25 mg) is obtained. m.p. >260° C., [α]$_D$=+7.9 (c=2, methanol), NMR (TMS, D$_2$O): 1.25÷1.40 (m, 2H), 1.42÷1.72 (m, 2H); 1.8÷2.06 (m, 2H); 2.9÷3.2 (m, 4H); 3.65 (t, 4H); 4.0 (t, 4H); 4.1 (t, 1H); 7.35 (s, 4H).

HPLC: Partisfere® C$_{18}$, 150×4.6 mm; 0.025M sodium heptanesulfonate in water/acetonitrile/dioxane 70:20:10, pH ~2.5 with H$_3$PO$_4$; flow 1.3 ml/min.; λ=255 nm. Retention time: 4.61'.

EXAMPLE 6

Following the same procedure as described in Example 5, by reacting the trisodium salts of the acids described in Example 2, the following acid monohydrochloride salts are obtained:

N-{4-[bis(2-chloroethyl)amino]-(L)-phenylalanyl}-4-amino-1-hydroxybutane-1,1-diphosphonic acid: NMR (D$_2$O, TMS): δ=1.6 (m, 2H); 1.92 (m, 2H); 3.15 (m, 4H); 3.65 (t, 4H); 4.0 (t, 4H); 4.1 (m, 1H); 7.35 (s, 4H);

N-{4-[bis(2-chloroethyl)amino]-(L)-phenylalanyl}-3-amino-1-hydroxypropane-1,1-diphosphonic acid: NMR (D$_2$O, TMS): δ=2,1 (m, 2H); 3,15 (m, 4H); 3,65 (t, 4H); 4,0 (t, 4H); 4,1 (m, 1H); 7,35 (s, 4H);

N-{4-[bis(2-chloroethyl)amino]-(L)-phenylalanyl}-6-amino-1-hydroxyhexane-1,1-diphosphonic acid: NMR (D$_2$O, TMS): δ=1.5 (m, 2H); 1.6 (m, 4H); 1.9 (m, 2H); 3.15 (m, 4H); 3.65 (t, 4H); 4.0 (t, 4H); 4.1 (m, 1H); 7.35 (s, 4H);

N-{4-[bis(2-chloroethyl)amino]-(L)-phenylalanyl}-4-amino-1-hydroxypentane-1,1-diphosphonic acid: NMR (D$_2$O, TMS): δ=1.4 (m, 3H); 1.7 (m, 2H); 1.9 (m, 2H); 3.15 (m, 3H); 3.65 (t, 4H); 4.0 (t, 4H); 4.1 (m, 1H); 7.35 (s, 4H);

N-{4-[bis(2-chloroethyl)amino]-(L)-phenylalanyl}-3-(2-aminocyclopent-1-yl)-1-hydroxypropane-1,1-diphosphonic acid: NMR (D$_2$O, TMS): δ=1.5 (m, 8H); 1.6 (m, 2H); 1.9 (m, 2H); 3.15 (t, 2H); 3.65 (t, 4H); 4.0 (t, 4H); 4.1 (m, 1H); 7.35 (s, 4H);

N-{4-[bis(2-chloroethyl)amino]-(L)-phenylalanyl}-4-amino-4,4-pentamethylene-1-hydroxybutane-1,1-diphosphonic acid: NMR (D$_2$O, TMS): δ=1.45 (m, 10H); 1.6 (m, 2H); 1.9 (m, 2H); 3.15 (m, 4H); 3.65 (t, 4H); 4.0 (t, 4H); 4.1 (m, 1H); 7.35 (s, 4H);

N-methyl-N-{4-[bis(2-chloroethyl)amino]-(L)-phenylalanyl}-5-amino-1-hydroxypentane-1,1-diphosphonic acid: NMR (D₂O, TMS): δ=1.55 (m, 4H); 1.9 (m, 2H); 2.1 (s, 3H); 3.05 (t, 2H); 3.15 (t, 2H); 3.65 (t, 4H); 4.0 (t, 4H); 4.1 (m, 1H); 7.35 (s, 4H);

N-{4-[bis(2-chloroethyl)amino]-(L)-phenylalanyl}-4-amino-4,4-tetramethylene-1-hydroxybutane-1,1-diphosphonic acid: NMR (D₂O, TMS): δ=1.5 (m, 8H); 1.6 (m, 2H); 1.9 (m, 2H); 3.15 (t, 2H); 3.65 (t, 4H); 4.0 (t, 4H); 4.1 (m, 1H); 7.35 (s, 4H).

EXAMPLE 7

A solution of 4-[bis(2-chloroethyl)amino]-(L)-phenylalanine (150 mg) in formic acid (1.82 ml) and acetic anhydride (0.64 ml) is stirred at room temperature for 3 hours. The reaction mixture is concentrated to reduced volume under reduced pressure and partitioned between water (3 ml) and ethyl acetate (2×50 ml). The organic phase is dried over sodium sulphate and the solvent is evaporated under vacuum, to give N-formyl-4-[bis(2-chloroethyl)amino]-(L)-phenylalanine (160 mg) as a yellow foam, $[\alpha]_D = +67°$ (C=2, ethanol).

NMR (CDCl₃, TMS): =2.9÷3.1 (m, 2H); 3.6 (m, 8H); 4.68÷4.79 (m, 1H); 6.5 (m, 2H+1H); 6.69 (d, 2H); 8.1 (s, 1H).

Following the same procedure as described in Example 1b) and 1c), this compound is transformed into the hydroxysuccinimido ester (50 mg) and then is reacted with 4-amino-1-hydroxybutane-1,1-diphosphonic acid (24.1 mg), to obtain N-{N'-formyl-4-[bis(2-chloroethyl)amino]-(L)-phenylalanyl}-4-amino-1-hydroxybutane-1,1-diphosphonic acid trisodium salt (32 mg); $[\alpha]_D = +7.5°$ (c=2, water)

NMR (D₂O, TMS): δ=1.7÷2.0 (m, 4H); 2.9÷3.1 (m, 2H); 3.2 (m, 2H); 3.75 (s, 8H); 4.55 (t, 1H); 6.85 (d, 2H); 7.15 (d, 2H); 8.05 (s, 1H).

HPLC: Partisfere ® C₁₈, 150×4.6 mm; 0.025M sodium heptanesulfonate in water/acetonitrile/dioxane 70:20:10, pH ~2.5 with H₃PO₄; flow 1.3 ml/min.; λ=255 nm. Retention time: 2.9'.

EXAMPLE 8

Following the same procedure as described in Example 1c), by reacting N-formyl-4-[bis(2-chloroethyl)amino]-(L)-phenylalanine hydroxysuccinimido ester with the appropriate aminoalkyl-1-hydroxy-1,1-diphosphonic acids, the following compounds are obtained:

N-{N'-formyl-4-[bis(2-chloroethyl)amino]-(L)-phenylalanyl}-5-amino-1-hydroxypentane-1,1-diphosphonic acid trisodium salt;

NMR (D₂O, TMS): δ=1.4÷1.6 (m, 4H); 1.92 (m, 2H); 2.9÷3.1 (m, 2H); 3.2 (m, 2H); 3.75 (s, 8H); 4.55 (t, 1H); 6.85 (d, 2H); 7.15 (d, 2H); 8.05 (s, 1H);

N-{N'-formyl-[4-bis(2-chloroethyl)amino]-(L)-phenylalanyl}-3-amino-1-hydroxypropane-1,1-diphosphonic acid trisodium salt;

NMR (D₂O, TMS): δ=2,1 (m, 2H); 2,9÷3,1 (m, 2H); 3,2 (m, 2H); 3,75 (s, 8H); 4,55 (t, 1H); 6,85 (d, 2H); 7,15 (d, 2H); 8,05 (s, 1H);

N-{N'-formyl-4-[bis(2-chloroethyl)amino]-(L)-phenylalanyl}-6-amino-1-hydroxyhexane-1,1-diphosphonic acid trisodium salt;

NMR (D₂O, TMS): δ=1.5 (m, 2H); 1.9 (m, 2H); 2.9÷3.1 (m, 2H); 3.2 (m, 2H); 3.75 (s, 8H); 4.2 (t, 1H); 6.85 (d, 2H); 7.15 (d, 2H); 8.05 (s, 1H);

N-{N'-formyl-4-[bis(2-chloroethyl)amino]-(L)-phenylalanyl}-4-amino-1-hydroxypentane-1,1-diphosphonic acid trisodium salt;

NMR (D₂O, TMS): δ=1.4 (d, 3H); 1.7 (m, 2H); 1.9 (m, 2H); 2.9÷3.1 (m, 2H); 3.2 (m, 2H); 3.75 (s, 8H); 4.55 (t, 1H); 6.85 (d, 2H); 7.15 (d, 2H); 8.05 (s, 1H);

N-{N'-formyl-4-[bis(2-chloroethyl)amino]-(L)-phenylalanyl}-3-(2-aminocyclopent-1-yl)-1-hydroxypropane-1,1-diphosphonic acid trisodium salt;

NMR (D₂O, TMS): δ=1.42÷1.75 (m, 9H); 1.9 (m, 2H); 2.9÷3.1 (m, 2H); 3.3 (m, 1H); 3.75 (s, 8H); 4.55 (t, 1H); 6.85 (d, 2H); 7.15 (d, 2H); 8.05 (s, 1H);

N-{N'-formyl-4-[bis(2-chloroethyl)amino]-(L)-phenylalanyl}-4-amino-4,4-tetramethylene-1-hydroxybutane-1,1-diphosphonic acid trisodium salt;

NMR (D₂O, TMS): δ=1.5 (m, 8H); 1.6 (m, 2H); 1.9 (m, 2H); 2.9÷3.1 (m, 2H); 3.75 (s, 8H); 4.55 (t, 1H); 6.85 (d, 2H); 7.15 (d, 2H); 8.05 (s, 1H);

N-{N'-formyl-4-[bis(2-chloroethyl)amino]-(L)-phenylalanyl}-4-amino-4,4-pentamethylene-1-hydroxybutane-1,1-diphosphonic acid trisodium salt;

NMR (D₂O, TMS): δ=1.45 (m, 10H); 1.6 (m, 2H); 1.9 (m, 2H); 2.9÷3.1 (m, 2H); 3.75 (s, 8H); 4.55 (t, 1H); 6.85 (d, 2H); 7.15 (d, 2H); 8.05 (s, 1H);

N-methyl-N-{N'-formyl-4-[bis(2-chloroethyl)amino]-(L)-phenylalanyl}-5-amino-1-hydroxypentane-1,1-diphosphonic acid trisodium salt;

NMR (D₂O, TMS): δ=1.55 (m, 4H); 1.9 (m, 2H); 2.1 (s, 3H); 2.9÷3.1 (m, 2H); 3.2 (m, 2H); 3.75 (s, 8H); 4.55 (t, 1H); 6.85 (d, 2H); 7.15 (d, 2H); 8.05 (s, 1H);

EXAMPLE 9

A solution of N-{N'-formyl-4-[bis(2-chloroethyl)amino]-(L)phenylalanyl}-4-amino-1-hydroxybutane-1,1-diphosphonic acid trisodium salt (32 mg) in methanol saturated with hydrochloric acid (1 ml) is heated to 40°-50° C. for 4 hours, then the solution is concentrated to reduced volume and the precipitated sodium chloride is filtered. The filtrate is evaporated to dryness and the residue is triturated with acetone and filtered. After recrystallization from ethanol/ethyl ether, N-{4-[bis(2-chloroethyl)amino]-(L)-phenylalanyl}-4-amino-1-hydroxybutane-1,1-diphosphonic acid monohydrochloride (25 mg) is obtained, m.p. >260° C.; $[\alpha]_D = +7.8$ (c=2, methanol).

NMR (D₂O, TMS): δ=1.6 (m, 2H); 1.92 (m, 2H); 3.15 (m, 4H); 3.65 (t, 4H); 4.0 (t, 4H); 4.1 (m, 1H); 7.35 (s, 4H).

HPLC: Partisfere ® C₁₈, 150×4.6 mm; 0.025M sodium heptanesulfonate in water/acetonitrile/dioxane 70:20:10, pH ~2.5 with H₃PO₄; flow 1.3 ml/min.; λ=255 nm. Retention time: 4.24'.

EXAMPLE 10

A solution of 4-[4-[bis(2-chloroethyl)amino]phenyl]-butyric acid N-hydroxysuccinimido ester (73 mg) in DMF (1 ml) is dropped at room temperature into a stirred solution of 4-aminobutane-1,1-diphosphonic acid tetraethyl ester (52 mg) in DMF/water 5/1 (0.6 ml).

After 3 hours, the mixture is concentrated under reduced pressure and partitioned between a 5% sodium hydrogen carbonate solution (5 ml) and ethyl acetate (5 ml). After separation of the organic phase, the aqueous phase is further extracted with ethyl acetate (2×5 ml) and discarded; the combined organic extracts are dried over sodium sulphate and solvent is evaporated off under reduced pressure, to yield N-[4-[4-[bis(2-chloroethyl)amino]phenyl]butyroyl]-4-aminobutane-1,1-diphosphonic acid tetraethyl ester (90 mg) as a clear oil;

NMR (CDCl₃, TMS): δ=1.35 (t, 12H); 1.90 (t, 2H); 2.2 (t, 2H); 2.0÷2.5 (m, 5H); 2.55 (t, 2H); 3.45 (q, 2H);

3.65 (m, 8H); 4.20 (m, 8H); 6.51 (t, 1H); 6.61 (d, 2H); 7.1 (d, 2H).

EXAMPLE 11

Under a nitrogen atmosphere, a solution of iodotrimethylsilane (92 μl) in anhydrous dichloromethane (1 ml) is dropped at 0° C. into a solution of N-{4-[4-[bis(2-chloroethyl)amino]phenylbutyroyl}-4-aminobutane-1,1-diphosphonic acid tetraethyl ester (72 mg) in anhydrous dichloromethane (1 ml). The mixture is stirred for 2 hours at 0° C., then it is allowed to room temperature and subsequently treated with methanol (1 ml). After 15 minutes, the solvent is evaporated off under reduced pressure and the residue is dissolved in water (2 ml), treated with 1N NaOH (0.228 ml) and extracted with ethyl acetate (2×2 ml). The organic extracts are discarded. The aqueous phase is diluted with DMF to yield a white solid which is recovered by centrifugation, to give N-{4-[4-[bis(2-chloroethyl)amino]phenyl]butyroyl}-4-aminobutane-1,1-diphosphonic acid disodium salt (45 mg);

NMR (D$_2$O, TMS): δ=1.9 (m, 6H); 2.25 (t, 2H); 2.55 (t, 2H); 3.38 (m, 2H); 3.72 (s, 8H); 6.85 (d, 2H); 7.2 (d, 2H).

EXAMPLE 12

Following the same procedure as described in Example 10, N-(tert-butoxycarbonyl)-4-[bis(2-chloroethyl)amino]-(L)-phenylalanine-N-hydroxysuccinimido ester (87,5 mg) is reacted with 4-aminobutane-1,1-diphosphonic acid tetraethyl ester (50 mg) to obtain N-{N'-(tert-butoxycarbonyl)-4-[bis(2-chloroethyl)amino]-(L)-phenylalanyl}-4-aminobutane-1,1-diphosphonic acid tetraethyl ester (87 mg) as a clear oil.

NMR (CDCl$_3$, TMS): δ=1.38 (m, 21H); 2.2 (m, 5H); 3.45 (m, 4H); 3.65 (m, 8H); 4.18 (m, 8H); 5.05 (m, 1H); 6.51 (t, 1H); 6.61 (d, 2H); 7.1 (d, 2H).

EXAMPLE 13

A solution of N-{N'-(tert-butoxycarbonyl)-4-[bis(2-chloroethyl)amino]-(L)-phenylalanyl}-4-aminobutane-1,1-diphosphonic acid tetraethyl ester (59 mg) in 10% HCl (1 ml) is heated to 45° C. for one hour, then evaporated to dryness under reduced pressure. The residue is suspended in ethyl ether (2 ml) and recovered by centrifugation, to give N-{[4-[bis(2-chloroethyl)amino]-(L)-phenylalanyl}-4-aminobutane-1,1-diphosphonic acid tetraethyl ester dihydrochloride (45 mg);

NMR (TMS, D$_2$O): δ=1.22 (t, 12H); 1.95 (m, 4H); 3.2 (m, 2H); 3.4 (m, 2H); 3.7 (t, 4H); 3.95 (m, 12H); 4.1 (t, 1H); 7.38 (s, 4H).

EXAMPLE 14

Under a nitrogen atmosphere, a solution of iodotrimethylsilane (134 μl) in anhydrous dichloromethane (1 ml) is dropped into a stirred solution of N-{N'-(tert-butoxycarbonyl)-4-[bis(2-chloroethyl)amino]-(L)-phenylalanyl}-4-aminobutane-1,1-diphosphonic acid tetraethyl ester (93 mg) in anhydrous dichloromethane (1 ml), cooled to 0° C.

The mixture is stirred for 2 hours, allowing it to warm to room temperature, then it is treated with methanol (1 ml). After 15 minutes, solvent is evaporated off under reduced pressure, the residue is dissolved in water, treated with 1N NaOH (0.254 ml) and extracted with ethyl acetate (2×3 ml). The organic extracts are discarded. The aqueous phase is diluted with DMF to precipitate a solid, which is recovered by centrifugation and washed with ethyl acetate.

45 mg of N-{4-[bis(2-chloroethyl)amino]-(L)-phenylalanyl}-4-aminobutane-1,1-diphosphonic acid disodium salt are obtained, NMR (D$_2$O, TMS): δ=1.95 (m, 4H); 2.9 (m, 2H); 3.4 (m, 2H); 3.65 (m, 1H); 3.75 (s, 8H); 6.88 (d, 2H); 7.18 (d, 2H).

EXAMPLE 15

Following the same procedures as described in Examples 12 and 13, using N-(tert-butoxycarbonyl)-4-[bis(2-chloroethyl)amino]-(L)-phenylalanine hydroxysuccinimido ester and the appropriate tetraalkylesters of aminoalkyl-1,1-diphosphonic acids the following compounds are prepared:

N-{4-[bis(2-chloroethyl)amino]-(L)-phenylalanyl}-3-aminopropane-1,1-diphosphonic acid tetraethylester dihydrochloride;

N-{4-[bis(2-chloroethyl)amino]-(L)-phenylalanyl}-5-aminopentane-1,1-diphosphonic acid tetraethylester dihydrochloride;

N-{4-[bis(2-chloroethyl)amino]-(L)-phenylalanyl}-6-aminohexane-1,1-diphosphonic acid tetraethylester dihydrochloride;

N-{4-[bis(2-chloroethyl)amino]-(L)-phenylalanyl}-4-aminopentane-1,1-diphosphonic acid tetraethylester dihydrochloride;

N-{4-[bis(2-chloroethyl)amino]-(L)-phenylalanyl}-3-(2-aminocyclopent-1-yl)propane-1,1-diphosphonic acid tetraethylester dihydrochloride;

N-{4-[bis(2-chloroethyl)amino]-(L)-phenylalanyl}-4-amino-4,4-tetramethylene-butane-1,1-diphosphonic acid tetraethylester dihydrochloride;

N-{4-[bis(2-chloroethyl)amino]-(L)-phenylalanyl}-4-amino-4,4-pentamethylene-butane-1,1-diphosphonic acid tetraethylester dihydrochloride;

N-methyl-N-4-[bis(2-chloroethyl)amino]-(L)-phenylalanyl}-5-aminopentane-1,1-diphosphonic acid tetraethylester dihydrochloride;

EXAMPLE 16

Following the same procedures as described in Example 1a) and 1b), 3-[bis(2-chloroethyl)amino]-(L)-phenylalanine (J. Med. Chem., 6, 85, (1963)) is transformed into N'-(tert-butoxycarbonyl)-3-[bis(2-chloroethyl)amino]-(L)-phenylalanine hydroxysuccinimido ester, which is reacted with 5-amino-1-hydroxypentane-1,1-diphosphonic acid following the procedure described in Example 1c), to give N-{N'-(tert-butoxycarbonyl)-3-[bis(2-chloroethyl)amino]-(L)-phenylalanyl}-5-amino-1-hydroxypentane-1,1-diphosphonic acid trisodium salt.

This compound is subsequently transformed into N-{3-[bis(2-chloroethyl)amino]-(L)-phenylalanyl}-5-amino-1-hydroxypentane-1,1-diphosphonic acid dihydrochloride, following the procedure described in Example 5.

EXAMPLE 17

Following the procedure described in Example 1a) and 1b), $N^6,N^6$-bis(2-chloroethyl)-(DL)-lysine (J. Med. Chem. 7, 468, (1964)) is transformed into $N^2$-(tert-butoxycarbonyl)-$N^6,N^6$-bis(2-chloroethyl)-(DL)-lysine hydroxysuccinimido ester which is reacted with 4-amino-1-hydroxybutane-1,1-diphosphonic acid, following the procedure described in Example 1c), to give N-[$N^2$-(tertbutoxycarbonyl)-$N^6,N^6$-bis(2-chloroethyl)-

(DL)-lysinyl]-4-amino-1-hydroxybutane-1,1-diphosphonic acid trisodium salt, which is in its turn transformed into N-[N⁶,N⁶-bis(2-chloroethyl)-(DL)-lysinyl]-4-amino-1-hydroxybutane-1,1-diphosphonic acid dihydrochloride, following the procedure described in Example 5.

EXAMPLE 18

Following the procedure described in Example 1b), by reacting 4-[2-[bis(2-chloroethyl)amino]phenyl]-butyric acid (J. Org. Chem. 26, 1554, (1961)) with N-hydroxysuccinimide and N-morpholinoethylisonitrile, 4-[2-[bis(2-chloroethyl)amino]phenyl]butyric acid N-hydroxysuccinimido ester is prepared. Said N-hydroxysuccinimido ester is reacted with 4-aminobutane-1,1-diphosphonic acid tetraethyl ester, according to the procedure described in Example 10, to give N-{4-[2-[bis(2-chloroethyl)amino]phenyl]butyroyl}-4-aminobutane-1,1-diphosphonic acid tetraethyl ester, which is reacted with iodotrimethylsilane, following the procedure described in Example 11, to obtain N-{4-[2-[bis(2-chloroethyl)amino]phenyl]butyroyl}-4-aminobutane-1,1-diphosphonic acid disodium salt.

We claim:

1. Compounds of formula (I)

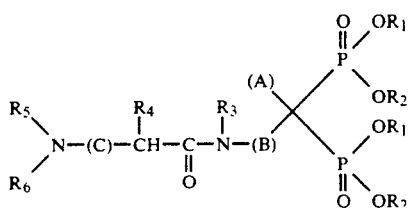

wherein:

$R_1$ and $R_2$, which can be the same or different, are hydrogen or $C_1$–$C_4$ alkyl;

(A) is hydrogen or hydroxy, (B) is a straight or branched $C_1$–$C_8$ alkylene or, together with the adjacent nitrogen atom, a group of formula

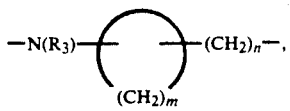

wherein the groups $N(R_3)$ and $(CH_2)_n$ may be in the 1,1; 1,2; 1,3; or 1,4 position of the ring;

m is the integer 5 or 6;

n is an integer 1 to 5;

$R_3$ is hydrogen, straight or branched $C_1$–$C_9$ alkyl;

(C) is straight or branched $C_1$–$C_5$ alkylene, phenylene, an aralkylene chain of formula

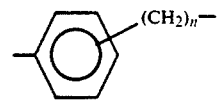

in which n is as above defined;

$R_4$ is hydrogen or a group of formula

in which $R_7$ and $R_8$, which are the same or different, are hydrogen, straight or branched $C_1$–$C_6$ alkyl, or one of $R_7$ and $R_8$ is as above defined and the other one is a group of formula

in which $R_9$ is hydrogen, straight or branched $C_1$–$C_4$ alkoxy; $R_5$ and $R_6$ are 2-haloethyl or $R_5$ and $R_6$, together with the nitrogen atom to which they are bound, are a 1-aziridinyl residue of formula

and isomers, diastereoisomers, and pharmaceutically acceptable salts thereof.

2. Compounds as claimed in claim 1, wherein A is hydroxy.

3. Compounds as claimed in claim 1, wherein A is hydrogen.

4. Compounds as claimed in claim 1, wherein $R_1$ and $R_2$ are hydrogen.

5. Compounds as claimed in claim 1, wherein $R_1$ and $R_2$ are $C_1$–$C_4$ alkyl.

6. Compounds as claimed in claim 1, wherein (B) is a $C_2$–$C_5$ alkylene chain and $R_3$ is hydrogen.

7. Compounds as claimed in claim 1, wherein (B) is a chain of formula

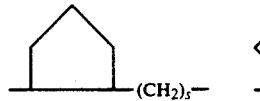 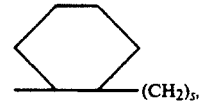

wherein s is from 1 to 4.

8. Compounds as claimed in claim 1, wherein (C) is phenylene or benzyl and $R_5$ and $R_6$ are 2-chloroethyl.

9. Compounds as claimed in claim 8, wherein (C) is benzyl and $R_4$ is amino, t-butoxycarbonylamino, formylamino, acetylamino, benzyloxycarbonylamino or ethoxycarbonylamino.

10. Compounds as claimed in claim 8, wherein (C) is phenthylene and $R_4$ is hydrogen.

11. Pharmaceutical composition suitable for use in tumor therapy comprising at least one compound of claim 1 and a nontoxic carrier.

* * * * *